(12) United States Patent
Bobroff (10) Patent No.: US 6,190,344 B1
(45) Date of Patent: Feb. 20, 2001

(54) ORTHOPAEDIC SUPPORT FASTENING SYSTEM

(75) Inventor: Alec Dimitry Bobroff, Oak Park, CA (US)

(73) Assignee: ADBME Enterprises Inc., Torrance, CA (US)

(*) Notice: Under 35 U.S.C. 154(b), the term of this patent shall be extended for 0 days.

(21) Appl. No.: 09/191,265

(22) Filed: Nov. 12, 1998

(51) Int. Cl.[7] .................... A61F 5/00; A61F 13/00
(52) U.S. Cl. .................................. 602/21; 602/64
(58) Field of Search .................. 602/20–22, 60–64; 118/878–880; 2/16, 20

(56) References Cited

U.S. PATENT DOCUMENTS

| | | | |
|---|---|---|---|
| 949,716 | * 2/1910 | Quenzer | 602/75 |
| 4,013,070 | * 3/1977 | Harroff | 602/21 |
| 4,215,687 | * 8/1980 | Shaw | 602/60 |
| 4,441,490 | * 4/1984 | Nirschl | 602/21 |
| 4,996,979 | * 3/1991 | Grim et al. | 602/21 |
| 5,058,576 | * 10/1991 | Grim et al. | 602/21 |
| 5,356,371 | * 10/1994 | Hubbard | 602/21 |

\* cited by examiner

*Primary Examiner*—Mickey Yu
*Assistant Examiner*—Denise Pothrer
(74) *Attorney, Agent, or Firm*—Townsend & Banta

(57) ABSTRACT

An orthopaedic support fastening system which incorporates a "one-size-fits-all" concept for support of various human limbs. The design itself comprises a substantially flat sheet of sheet material having extending straps and slot apertures. The slot apertures, used for receiving straps, provide increased stability and support once the limb is properly positioned. The preferred means of securing the straps to the support is by the use of hook and loop material although other means of attachment can be used such as snaps.

4 Claims, 8 Drawing Sheets

ORTHOPAEDIC SUPPORT FASTENING SYSTEM

TECHNICAL FIELD

The invention relates to orthopaedic supports and more particularly, to orthopaedic support devices which utilize single-size construction yet can be adjusted to fit a specific user's anatomy.

BACKGROUND OF THE INVENTION

Orthopaedic supports are typically used to stabilize and protect various limbs of the human anatomy from sustaining injury or increased injury. Typically, orthopaedic supports have been used on elbows, wrists, knees and ankles. The purpose of an orthopaedic support is to reduce strain on the injured or weakened limb while permitting the limb to continue its function; minimizing the risk of either a more damaging injury or a renewed injury. Some supports have included braces formed of hard plastic or metal to stabilize and restrict the range of motion of the limb.

In order for the orthopaedic support to properly function, it has been necessary for the support to be sized for the specific limb. As a result, orthopaedic supports have been manufactured in various sizes such as, small, medium, large, extra large, etc.

However, since orthopaedic supports are usually manufactured in pre-determined sizes, some individuals may not be able to enjoy the maximum protection offered by such a support because their personal physical characteristics do not fit one of the manufactured sizes. For example, a small-size support may be too tight, restricting blood flow and causing discomfort while a medium-sized support may be too loose to offer any worthwhile support.

Accordingly, there is a need for the manufacture of orthopaedic supports which can be custom fit for any wearer i.e. a self adjusting, one-size-fits-all configuration.

Statement of the Invention

The present invention provides for a self adjusting, one-size-fits-all orthopaedic support and fastening system. A self adjust sizing or, one-size-fits-all support is desirable in that it can substantially reduce the large inventory of various size product in doctor's offices and will also provide an effective support for a patient who is in-between sizes. Irregular sized patients will also have a product alternative.

The present invention also introduces a new fastening system which provides an easy method for securing the support device to a limb. This new fastening system is of great help to those presently having difficulty; such as the elderly.

The new fastening system is defined as being self-adjusting, one-size-fits-all in that any of the orthopaedic support devices according to the invention as described below can be properly secured to patients having different sizes of the same limb.

The self-adjusting, one-size-fits-all fastening system according to the invention utilizes, in general, the same technique on each type of support device. In general, a substantially flat pattern is provided.

First, a specific pattern is formed or cut is required for each type of orthopaedic support. Straps are used: (1) to establish the inside diameter of the support and (2) once the limb is in position, the straps are used to adjust the support inside diameter for proper fit and comfort, and thereafter the support is temporarily fastened about the specific limb. These straps extend away from the pattern. Also, slot apertures corresponding to specific straps are provided.

Each orthopaedic support can be adjusted to a patient's specific anatomy. This is accomplished by threading each strap through its corresponding slot, and thereafter wrapping each strap around the entire limb. Each strap is then secured to the support device.

The minimum number of straps used depends upon the type of orthopaedic support. For example a forearm support can be made utilizing a single strap whereas orthopaedic support for a joint such as a knee or elbow will require at least one strap on either side of the joint.

Although adhesive or snaps can be utilized, most preferably, the fastening means is a hook and loop material such as VELCRO®. The patient can determine whether the device is providing the necessary comfort or support and can readjust as necessary.

The support system of the invention provides a temporary fastening or securing means rather than a permanent fastening means. "Temporary fastening means" is defined as any fastening means which will stay fastened until released by human hand or instrument. In other words, engagement of the hook material with loop material is a temporary fastening means because it can be disengaged at any time by the wearer or someone assisting the wearer. The fastening means can be re-engaged repeatedly.

As required, the patient can adjust the tightness of the support about the limb until the desired comfort and support is attained.

Preferably, each slot is reinforced to prevent tearing and wear as the straps can be repeatedly inserted and removed.

In addition to customizing the fastening component, this invention allows for the inclusion of adjustable hardware (hinges, stays, etc.) by various temporary securing means of attachment such as snaps, straps, although most preferably, by a hook and loop material.

Depending on the specific portion of the anatomy, the fastening system could either be made for open application or closed application.

"Open application" is defined as meaning that the device, to be used, is wrapped about the limb and thereafter secured or fastened as described above and, in more detail later.

"Closed application" is defined as meaning that the device is partially fastened to itself, so that generally a tubular aperture is formed before positioning about a limb. The device can then be slid past the hand (for wrist, forearm or elbow orthopaedic supports) or the foot (for ankle or knee orthopaedic supports) until the support is in the desired position about the injured limb. Once in position, each strap can be placed in tension, thereby reducing the inner diameter of the tubular aperture about the limb until the desired snugness and support are attained. The straps thereafter can be wrapped about the support and temporarily fastened.

A closed application permits the patient an easier procedure for securing the device to the limb. For example, the wrist support can be secured with only one hand for either the closed or open application. However, as will be discussed below, securing the device using the closed application is more desirable than with the open application.

With regard to materials, any type of sheet or roll material could be used to make the orthopedic supports of the invention. Leather, pack cloth, suede, and nylon can be used. Preferably, the supports are made from a closed-cell foam rubber such as neoprene which is stretchable; or from open-cell foam laminates such as foam laminated to cordura, medical brush, tricot, and fabrics. As to whether a support must possess an elastic or stretchable quality, it would be dependent on the type of support required for a particular type of limb. For example, a stretchable quality may not be necessary for a forearm or wrist as it would be necessary for an ankle or knee.

These and many other features and attendant advantages of the invention will become apparent as the invention becomes better understood by reference to the following detailed description when considered in conjunction with the accompanying drawings.

DETAILED DESCRIPTION OF THE INVENTION

Each of the orthopaedic support devices can be secured to the desired limb utilizing either the open or closed application. Because the orthopaedic support configurations vary according to the desired limb, preferred embodiments will be discussed for the knee, elbow, wrist and ankle. Although the configurations vary, the fastening system for each of the supports described below incorporate straps and slot apertures for configuring the flat sheet material into a general tubular shape.

I. KNEE ORTHOPAEDIC SUPPORT

Figure 1:
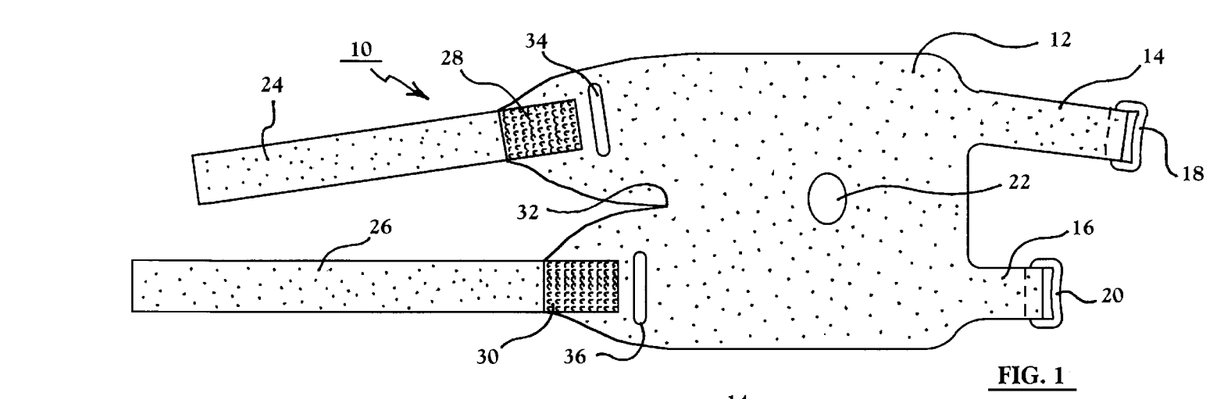
FIG. 1 is an exterior perspective view of an orthopaedic knee support in a flat, unused configuration.

Referring to FIG. 1, an orthopaedic support for the knee is generally shown at 10. Preferably, the knee support 10 comprises a main section 12, having a pair of integral straps 14 and 16 which extend away from main section 12. Main section 12 and straps 14 and 16 are preferably made from an elastic or stretchable material. Located at the distal end of strap 14 and strap 16 are D-rings 18 and 20 respectively. Main section 12 also has a circular aperture 22 which is used for properly positioning support 10 about a user's knee.

Located opposite main section 12 from integral straps 14 and 16 are a pair of straps 24 and 26. Strap 24 is permanently secured on a first end 28 to main section 12. Likewise, strap 26 is permanently secured on a first end 30 to main section 12. Any suitable means of securement can be utilized such as, but not limited to, adhesive or stitching.

A substantial portion of the side of first ends 28 and 30 which face away from main section 12 comprise hook material. The portions of straps 24 and 26 which are not attached to main section 12, each have a respective layer of loop material facing the same direction as the hook material as is illustrated in FIG. 1.

Between ends 28 and 30, the perimeter of main section 12 decreases to a point identified as 32. This configuration permits a higher degree of comfort and support when device 10 is wrapped about a knee than if the perimeter was not reduced.

A pair of slots 34 and 36 are also formed in or cut from main section 12. Each slot is located generally near respective attached first ends 28 and 30.

A. OPEN APPLICATION

Figures 2, 6:
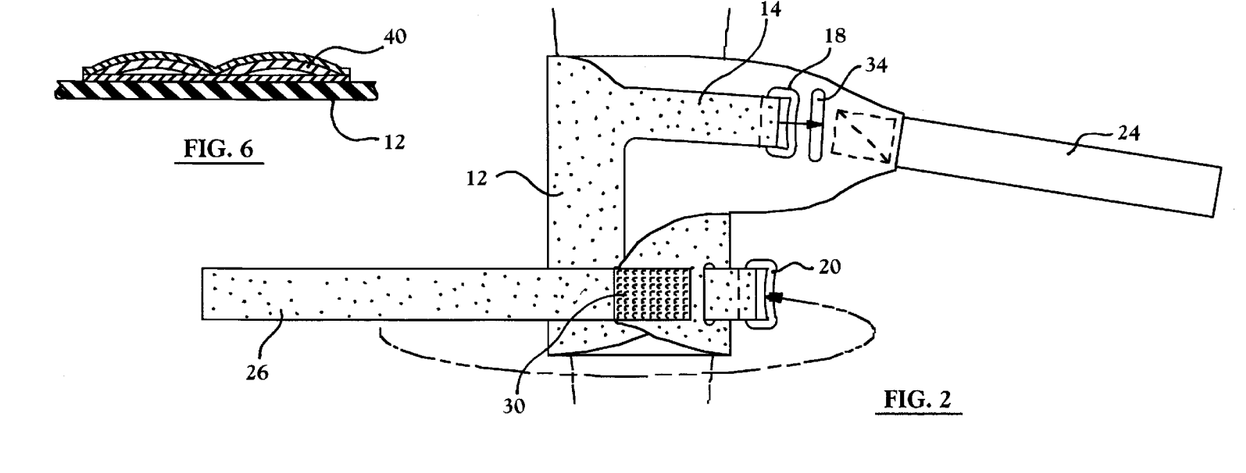
FIG. 2 illustrates the orthopaedic knee support of FIG. 1 being secured to a human knee.
FIG. 6 is a cross-sectional view of the support moldings of the alternative orthopaedic knee support of FIG. 5 taken along the line 6—6.
Figure 3:
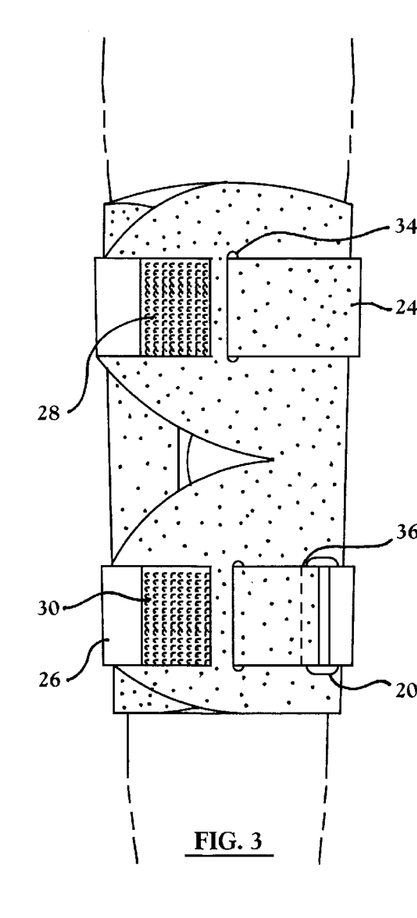
FIG. 3 illustrates a back view of the orthopaedic knee support of FIG. 1 secured to a human knee.
Figure 4:
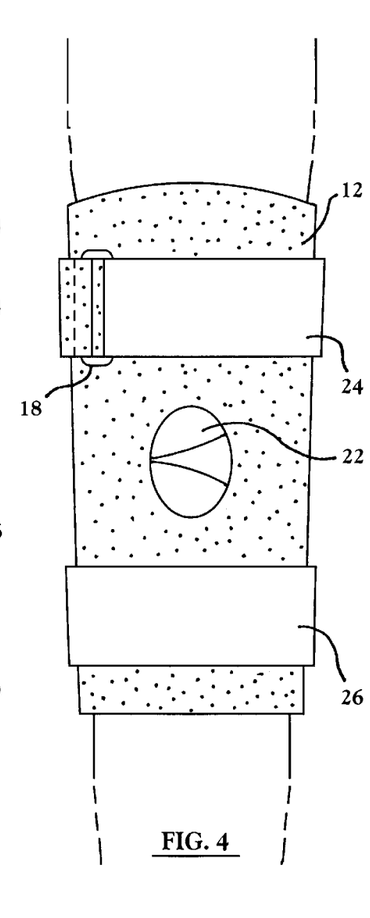
FIG. 4 illustrates a front view of the orthopaedic knee support of FIG. 1 secured to a human knee.

FIG. 2 illustrates the open application of knee support 10 to a patient's knee. Once aperture 22 is positioned about the knee cap, D-ring 18 is wrapped about the back of the knee and thereafter passed through slot 34. The same procedure passes D-ring 20 through slot 36. Once D-rings 18 and 20 are through their respective slots 34 and 36, as best shown in FIG. 2, strap 26 is wrapped over main section 12, passed through D-ring 20 and thereafter back across main section 12 until strap 26 can engage the hook material found on attached end 30. Because loop material is found on a substantial portion of strap 26, varying degrees of comfort and support can be achieved.

The same procedure is also used to secure the loop material on strap 24 to the hook material found on attached end 28. It should be noted that the positioning of the hook and loop material on straps 24 and 26 can be switched and no significance should be attached to the description presented here for the use of only hook material on first ends 28 and 30.

B. CLOSED APPLICATION

The main difference between the previously described open application and the closed application is that knee support 10 is partially assembled, taking on a generally tubular shaped configuration which can thereafter be slid over the foot, ankle and calf until in position about the knee. To obtain the tubular shaped configuration, D-rings 18 and 20 are passed through their respective slots 34 and 36 as described above for the open application.

It should be noted that in the preferred embodiment, the opening for slots 34 and 36 are larger than straps 14 and 16 but smaller than the outside configuration of D-rings 18 and 20. Although larger than slots 34 and 36, D-rings 18 and 20 can still be inserted through slots 34 and 36 by angling slightly. Also, because of the elastic nature of the main body material, the opening of slots 34 and 36 may be temporarily enlarged slightly while D-rings 18 and 20 are passed through their respective slots 34 and 36. Once through, the oversized D-rings, relative to slots 34 and 36, prevent the inadvertent travel of D-rings back through their respective slots. The over-size D-rings therefore, ensure that the tubular configuration is maintained while the support is slid over foot, ankle and calf.

C. ALTERNATIVE DESIGNS

Figure 5:
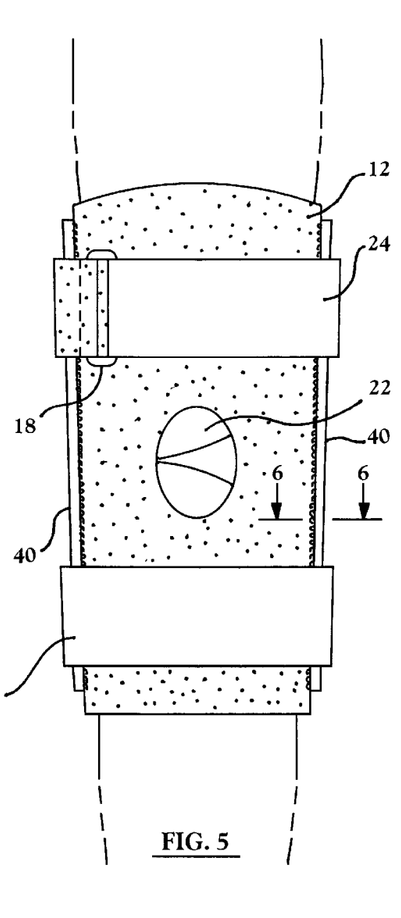
FIG. 5 illustrates an alternative to the secured orthopaedic knee support of FIG. 4 which incorporates support moldings.

FIG. 5 illustrates an alternative design of my knee support where support members 40 are provided for additional stabilization of the knee joint. Support members 40 can be made preferably of either a rigid molded material or metallic material such as steel. The means utilized for attaching support members 40 into position include adhesive or stitching in place. Most preferably, the attaching means utilize hook and loop material to attach support members 40 to main body 12 as is best illustrated in FIG. 6.

II. ELBOW ORTHOPAEDIC SUPPORT

Figure 7:
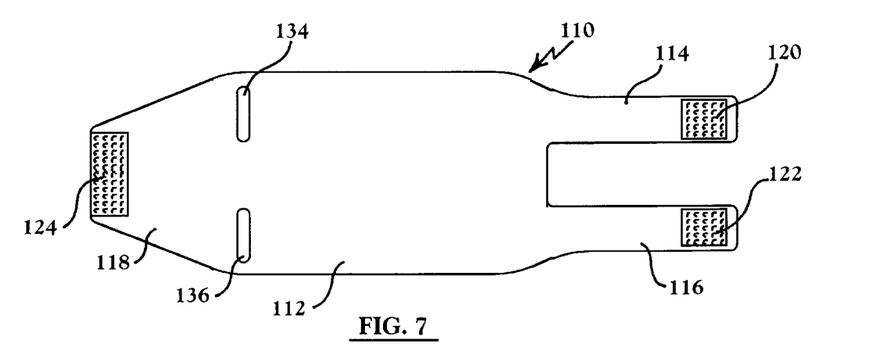
FIG. 7 is an exterior perspective view of an orthopaedic elbow support in a flat, unused configuration.

Referring to FIG. 7, the orthopaedic support according to the invention for the elbow is generally shown at 110. Preferably, elbow support 110 comprises a main section 112, having a pair of integral straps 114 and 116 which extend away from main section 112 on one side, and a tapered strap 118 extending away from main section 112 on the opposite side. At each distal end of straps 114, 116, and 118 is a layer of hook material shown as 120, 122, and 124 respectively. Facing away from the opposite side of main section 112 is a layer of loop material 126. Preferably, for ease of manufacture, the layer of loop material 126 substantially covers Main section 112 and straps 114 and 116. Preferably, the elbow support is constructed from an elastic or stretch material.

A pair of slots 134 and 136 are also formed in main section 112. Each slot is located in main section 112 generally near the beginning of tapered strap 118.

A. OPEN APPLICATION

Figure 8:
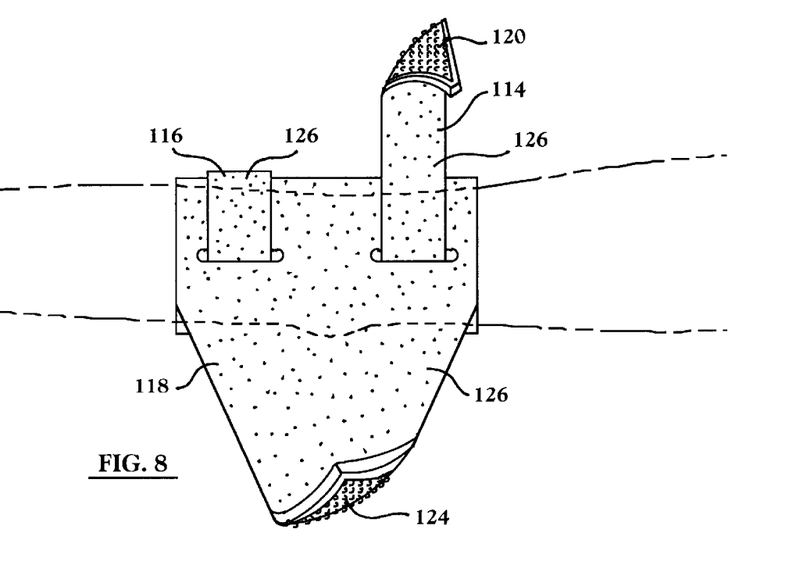
FIG. 8 illustrates the orthopaedic elbow support of FIG. 7 shown in an intermediate stage of being secured to a human elbow.
Figure 9:
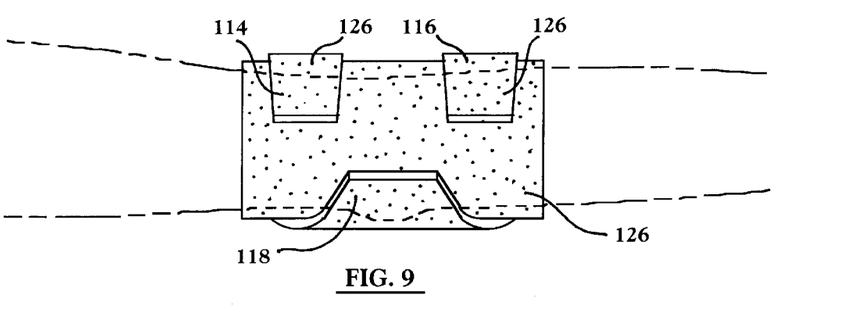
FIG. 9 illustrates the orthopaedic elbow support of FIG. 7 secured to a human elbow.

The patient's limb would be placed transversely across the elbow support shown in FIG. 8. Straps 114 and 116 would be wrapped about the elbow and then inserted through slots 134 and 136 respectively. After these straps pass through their corresponding slot, hook layers 120 and 122 can engage the loop material layer 126. Thereafter, tapered strap 118 is wrapped around the elbow with hook layer 124 engaging loop material layer 126. Once hook layers 120, 122, and 124 are secured to loop material layer 126, each hook layer can be released from engagement with material layer 126 and then re-engaged, to either tighten or loosen the support 110 about the patients elbow.

B. CLOSED APPLICATION

As discussed for the knee brace above, the main difference between the previously described open application and the closed application is that elbow support 110 is partially assembled, taking on a generally tubular shaped configuration which can thereafter be slid over the hand and wrist until in position about the elbow. To obtain the tubular shaped configuration, the distal ends of straps 114 and 116 are passed through their respective slots 134 and 136 as described above for the open application.

III. WRIST ORTHOPAEDIC SUPPORT

Figures 10, 12:
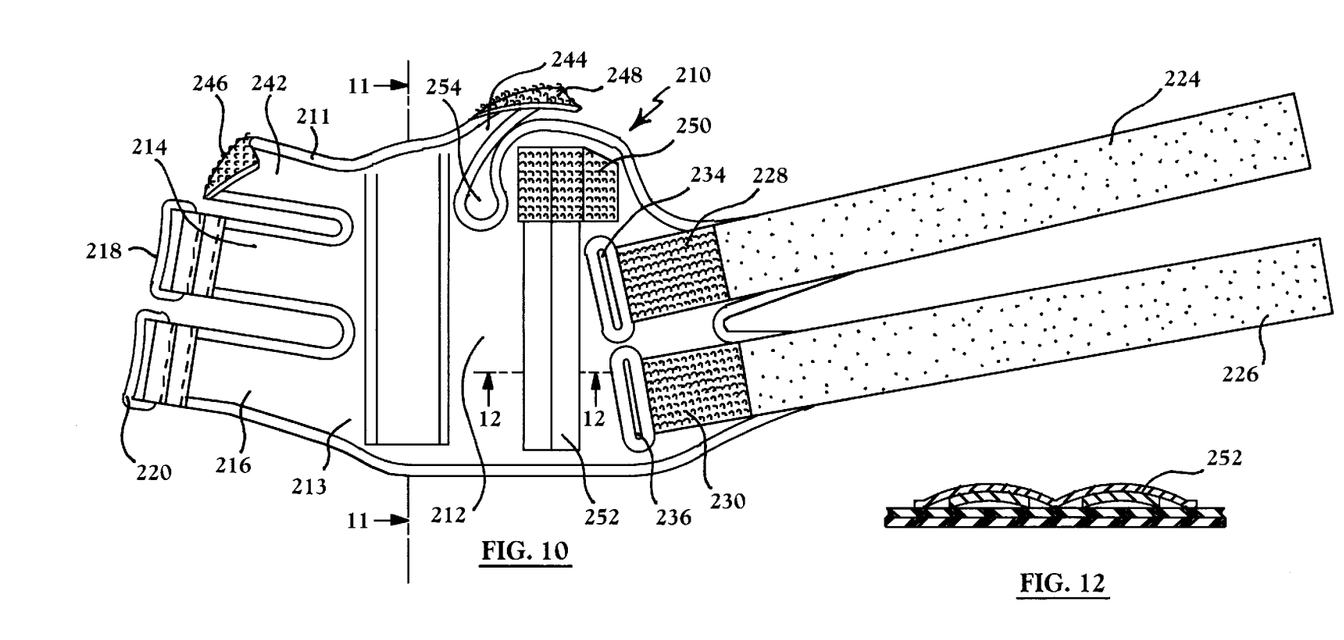
FIG. 10 is an exterior perspective view of an orthopaedic wrist support in a flat, unused configuration.
FIG. 12 is a cross-section of FIG. 10 taken along the line 12—12.

Referring to FIG. 10, an orthopaedic support according to the invention for the wrist is generally shown at 210. Preferably, wrist support 210 comprises a main section 212, having a pair of integral straps 214 and 216 which extend away from main section 212. Main section 212 is preferably comprised of a durable outer layer 213 and an inner layer 215. Inner layer 215 is made from non-abrasive material to provide comfort to the wearer's wrist. In addition, main section 212 is reinforced on its perimeter by a protective perimeter layer 211 which is preferably stitched into position although other means of attachment may be applied. Located at the distal end of strap 214 and strap 216 are D-rings 218 and 220 respectively.

Located opposite main section 212 from integral straps 214 and 216 are a pair of straps 224 and 226. Strap 224 is permanently secured on a first end 228 to main section 212. Likewise, strap 226 is permanently secured on a first end 230 to main section 212. Any suitable means of securement can be utilized such as, but not limited to, adhesive or stitching.

A substantial portion of the side of first ends 228 and 230 which face away from main section 212 comprise hook material. The portions of straps 224 and 226 which are not attached to main section 212, each have a respective layer of loop material facing the same direction as the hook material as is illustrated in FIG. 10.

Figure 11:
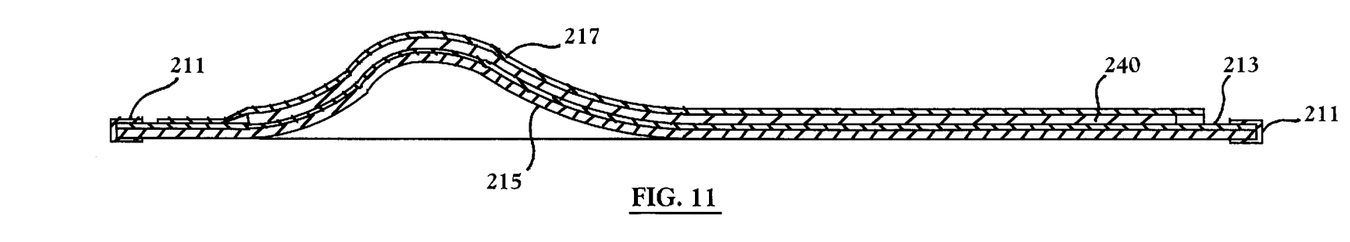
FIG. 11 is a cross-section of FIG. 10 taken along the line 11—11.

The wrist support 210 incorporates a brace member 240 which limits movement of the wrist in the upward/downward direction. Preferably, brace member 240 is shaped aluminum although any other material may be utilized which would immobilize the wrists upward/downward movement when support 210 is properly attached to a wrist. As best illustrated in FIG. 11, a pocket can be provided where brace member 240 is slid into position between the outside surface of outer layer 213 and the inside surface of pocket layer 217. Although brace member 240 may be permanently set within the pocket, it is preferred to have it removable so that its shape can be altered as necessary to provide optimum support and comfort for the wearer.

Extending away from main section 212 in the same general direction as straps 214 and 216 is an additional strap 242 which is also integral with main section 212. As shown on FIG. 10, secured to the distal end of strap 242 is an area of loop material 246.

Extending away from main section 212 is strap 244 which is also integral with main section 212. Secured to the distal end of strap 244 is an area of loop material 248. The open space between strap 244 and main body 212 defines a thumb channel 254 as shown in FIG. 10.

Located on the surface of main section 212 is a layer of hook material 250. Hook material 250 serves to temporarily secure straps 242 and 244 into position by engagement of their respective loop material distal ends 246 and 248. Engagement of straps 242 and 244 to hook material 250 serve to limit the lateral and upward/downward movement of the finger and knuckle area of the hand.

To provide additional resistance against the upward movement of the wrist relative to the elbow, support members 252 are provided by stitching into place above outer layer 213.

A. OPEN APPLICATION

The support shown in FIG. 10 is inverted so that soft layer 215 is facing the patient's wrist. The wearer's palm, wrist and forearm are placed transversely across my wrist support so that the limb is resting on soft layer 215, directly above brace member 240 and the wearer's thumb is aligned with thumb channel 254. Main body 212 would then be wrapped around the wrist to allow D-rings 218 and 220 to be inserted through slots 234 and 236 respectively. At this stage, distal end loop material 246 and 248 can be secured to hook material layer 250. Next, straps 224 and 226 are wrapped around the underside of the limb and thereafter inserted through D-rings 218 and 220 respectively. After insertion through the D-rings, straps 224 and 226 are wrapped back about the underside of the limb until the loop material of each strap can temporarily engage with hook material 228 or 230.

Once loop material layers 224 and 226 are secured to hook material 228 and 230 and loop material layers 246 and 248 are secured to hook material 250, each loop layer can be released from engagement with its respective hook material to either tighten or loosen the support 210 about the patients wrist before re-engagement.

B. CLOSED APPLICATION

As discussed for the knee brace above, the main difference between the previously described open application and the closed application is that wrist support 210 is partially assembled, taking on a generally tubular shaped configuration which can thereafter be slid over the hand and wrist until in position. To obtain the tubular shaped configuration, D-rings 218 and 220 located on the distal ends of straps 214 and 216 are passed through their respective slots 234 and 236 as described above for the open application.

The hand and wrist can then be slid through wrist support 210 until the wearer's thumb is positioned in thumb channel 254 and the palm and wrist are resting directly above brace member 240. Once in position, the straps are secured about the limb as discussed above for the open position.

C. ALTERNATIVE DESIGNS

Figures 13, 14, 15:
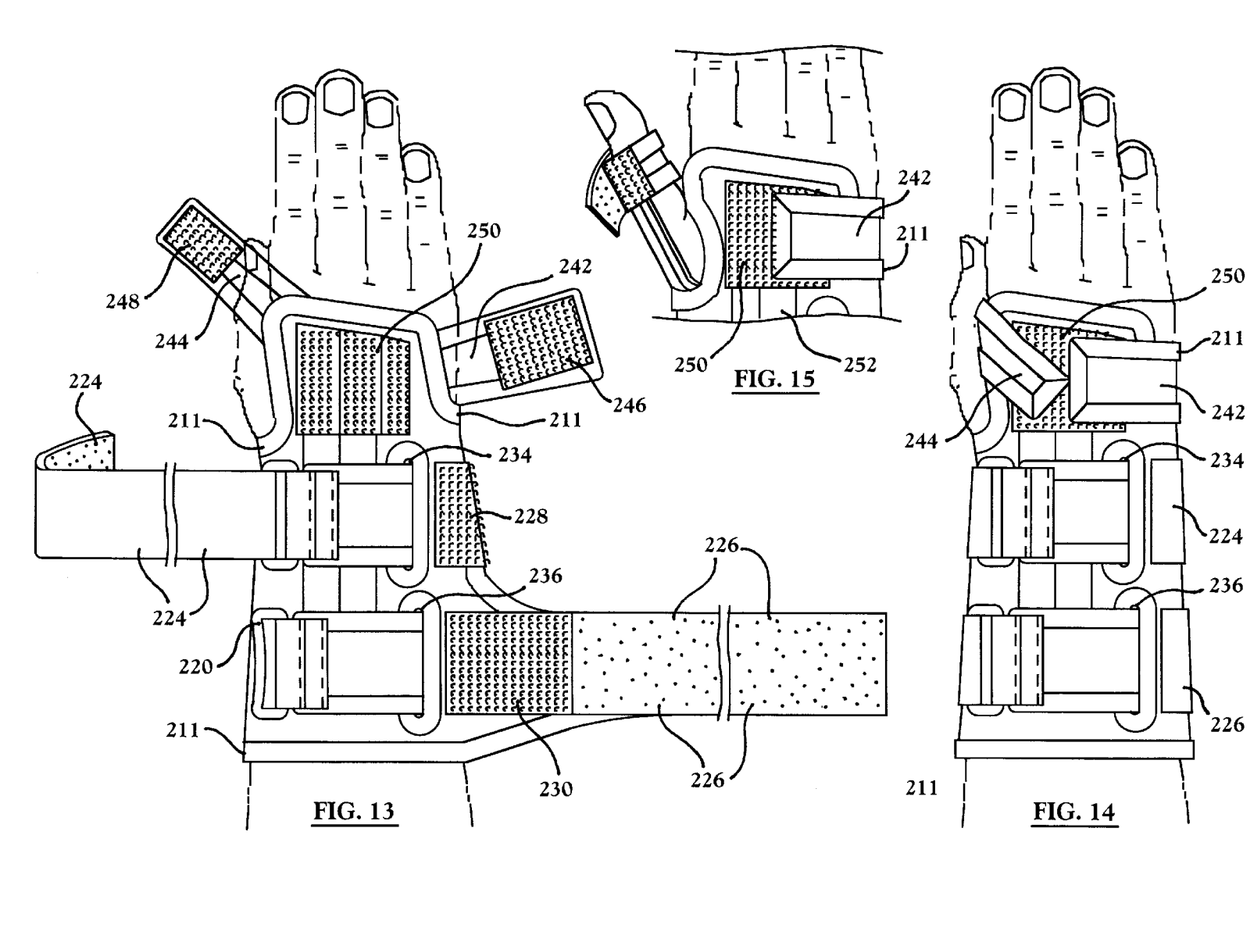
FIG. 13 illustrates the orthopaedic wrist support of FIG. 10 being shown being secured to a human wrist.
FIG. 14 illustrates the orthopaedic wrist support of FIG. 10 secured to a human wrist.
FIG. 15 illustrates an alternative to the orthopaedic wrist support of FIG. 10 where a human thumb is immobilized.

FIG. 15 illustrates an alternative design of a wrist support where a wearer's thumb can be immobilized in a fixed position by having the wearer's thumb wrapped as shown.

IV. ANKLE ORTHOPAEDIC SUPPORT

Figures 16, 17:
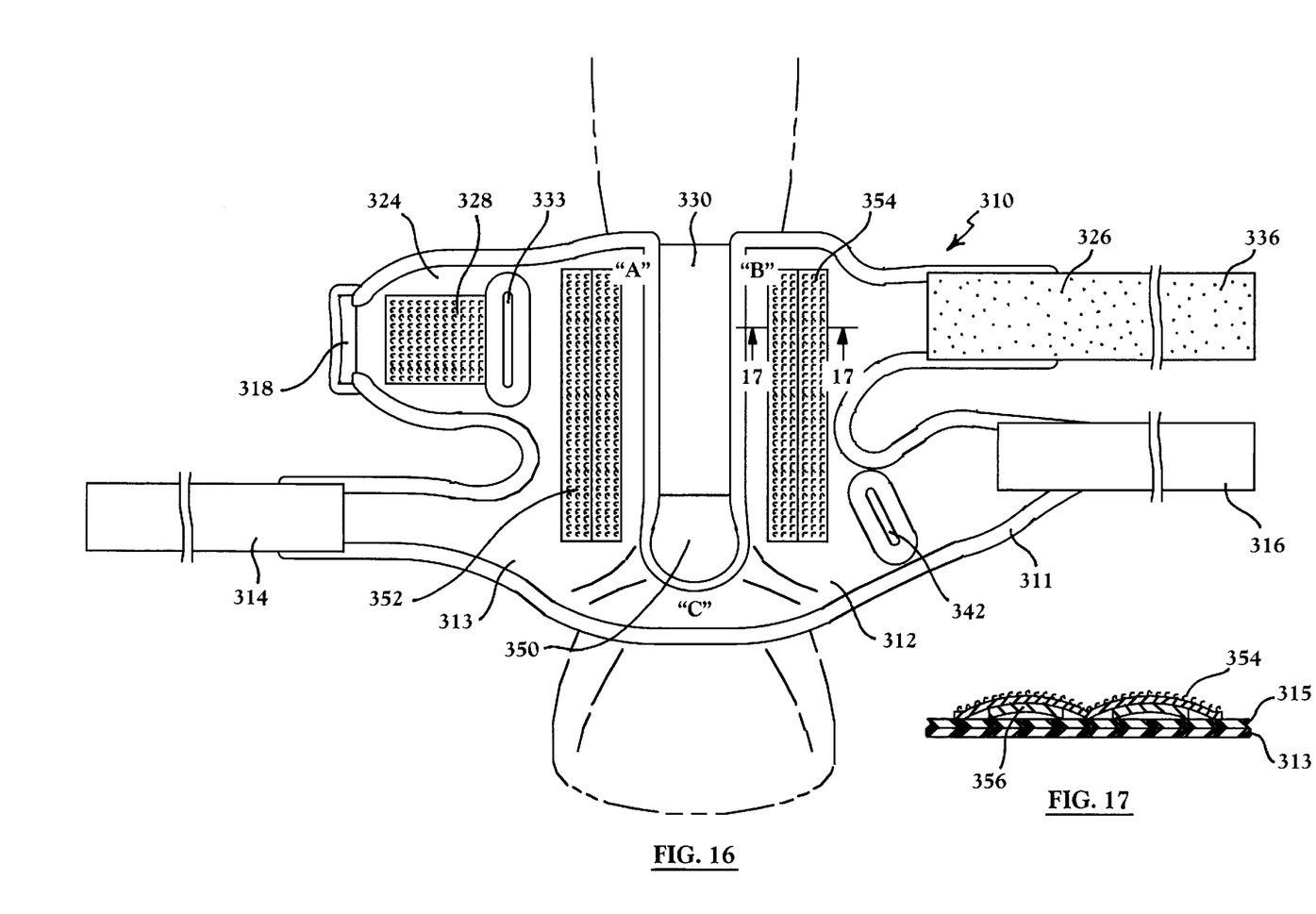
FIG. 16 is an exterior perspective view of an orthopaedic ankle support.
FIG. 17 is a cross-section of FIG. 16 taken along the line 17—17.

Referring to FIG. 16, an orthopaedic support for the ankle is generally shown at 310. Ankle support 310 comprises a shaped main section 312, and an elastic strip 330 which is secured on either side to facing perimeter portions of main section 312. Positioning of elastic strip 330 to main section 312 also creates a space or aperture 350 which is used to receive the wearer's heel. The attachment of elastic strip 330 to main section 312, provides a configuration whereby: a) elastic strip 330 will be aligned with the wearer's Achilles tendon; b) one portion of main section 312, defined as "A", will be aligned with one side of the wearer's ankle; c) a second portion of main section 312, defined as "B" will be aligned with the other side of the wearer's ankle; and d) a third portion of main section 312, defined as "C" will be aligned with the wearer's heel.

Figure 18:
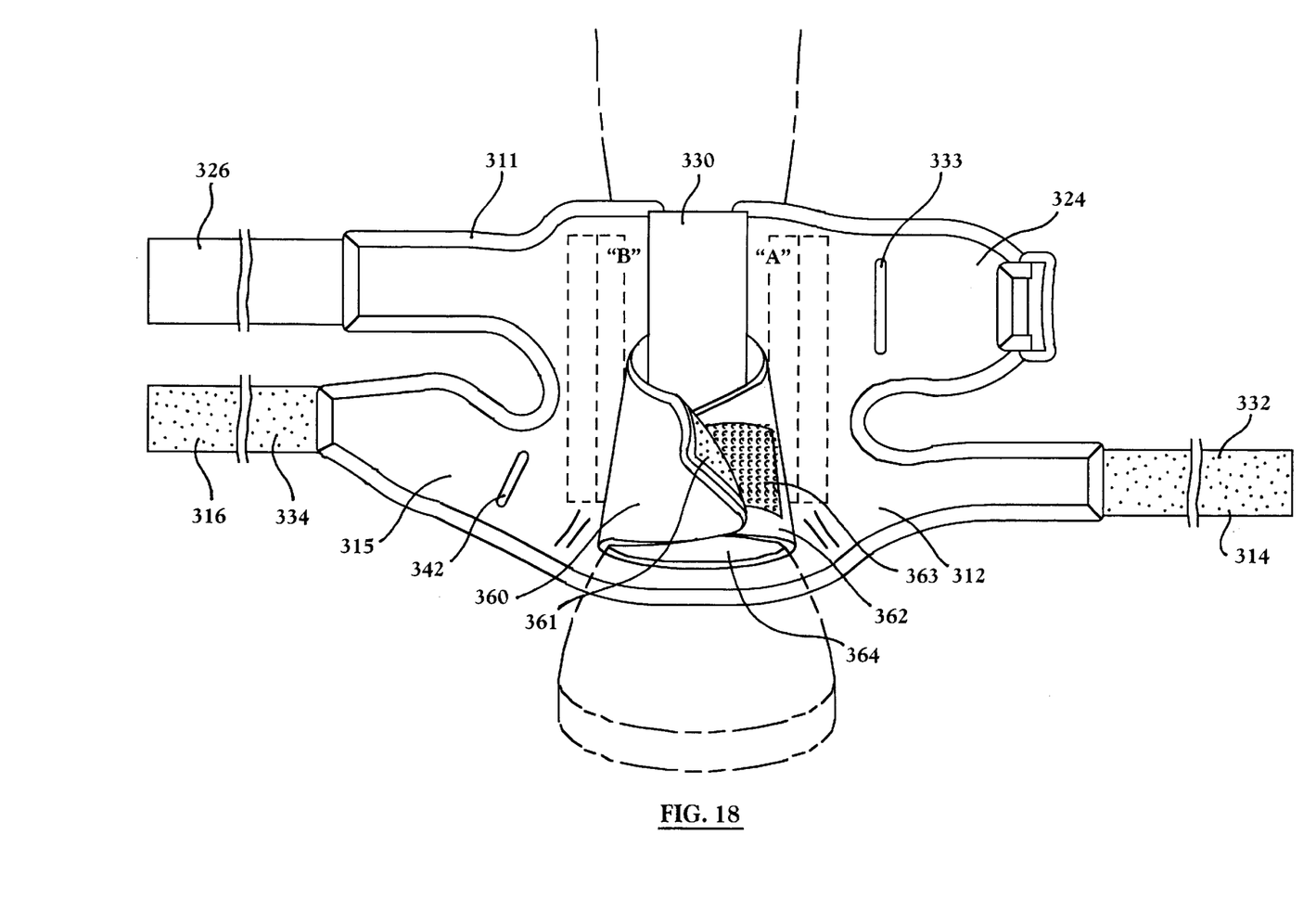
FIG. 18 illustrates the orthopaedic ankle support of FIG. 16 being secured to a human ankle.
Figure 19:
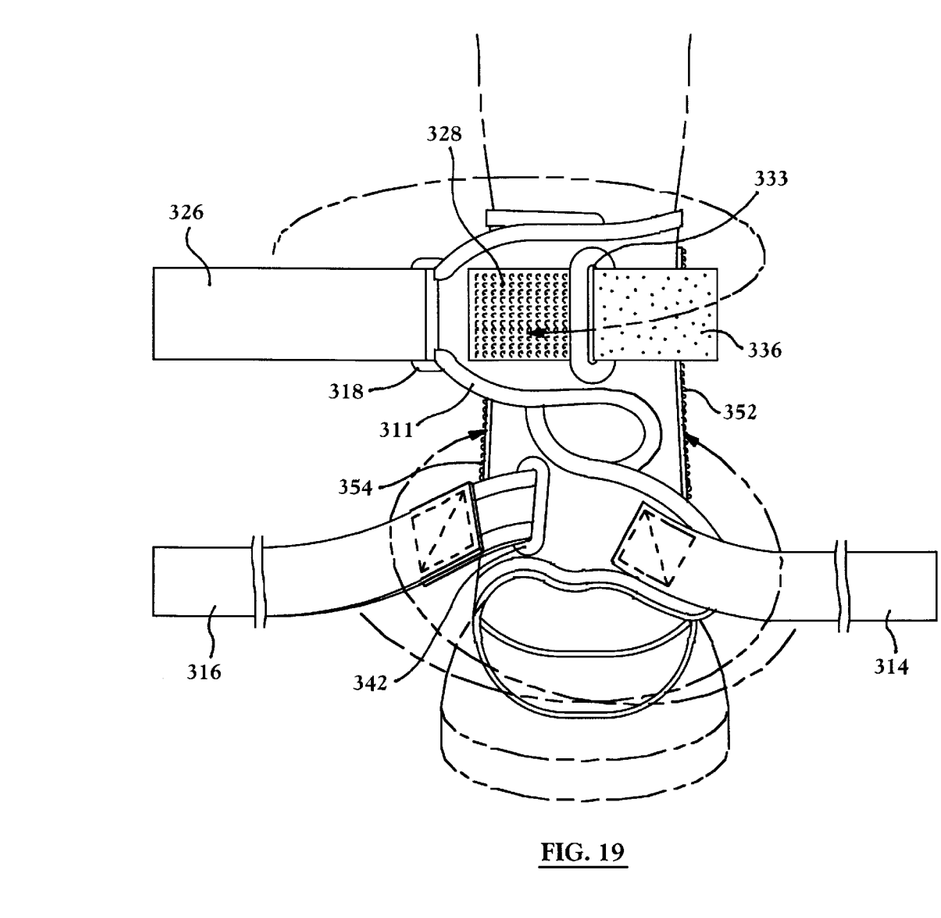
FIG. 19 illustrates the orthopaedic ankle support of FIG. 16 being shown in a second stage being secured to a human ankle.
Figure 20:
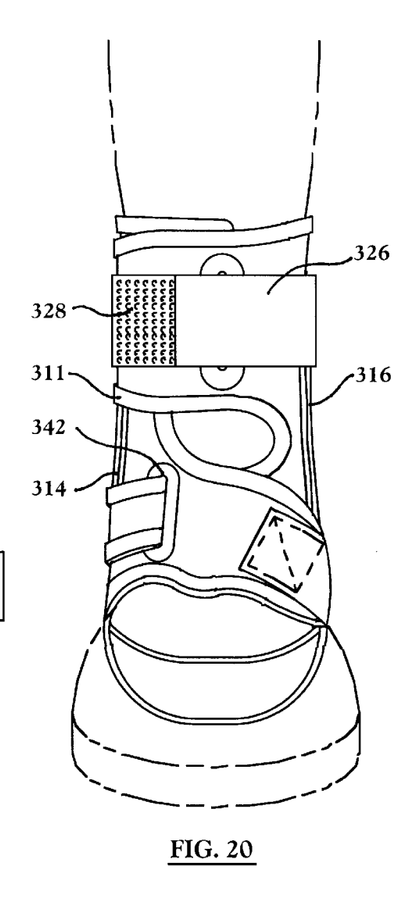
FIG. 20 illustrates the orthopaedic ankle support of FIG. 16 secured to a human ankle.

Extending away from main section 312 is a first pair of straps 314 and 316. As shown in FIG. 18, straps 314 and 316 each have a layer of loop material, 332 and 334 respectively. Located near strap 316 on main section 312 is a reinforced slot 342.

Main section 312 is preferably comprised of a durable outer layer 313 and an inner layer 315. Inner layer 315 is made from non-abrasive material to provide comfort to the wearer's ankle. In addition, main section 312 is reinforced on its perimeter by a protective perimeter layer 311 which is preferably stitched into position although other means of attachment may be alternatively used.

As best illustrated in FIG. 16, side "A" has an outer layer area of hook material 352. Similarly, side "B" also has an outer layer area of hook material 354. Straps 314 and 316 are respectively secured to hook material 352 and 354 as will be discussed below.

As shown by FIG. 16 and FIG. 17, a pair of support members 356 are disposed between hook material 352 and 354 and outer layer 313.

Located near the other end of main section 312 from straps 314 and 316 is a second pair of straps 324 and 326. Preferably, strap 324 is an integral extension from main section 312 and has a D-ring 318 attached to its distal end. Strap 324 also has an area of hook material 328 and a reinforced slot 333. Strap 326 is permanently secured to main section 312. As illustrated in FIG. 16, one side of strap 326 comprises a layer of loop material 336. As will be described shortly, strap 326 will be secured about the limb slightly above the ankle by engagement of loop material 336 with hook material 328.

As is best shown in FIG. 18, the ankle support 310 uses a third pair of straps indicated as 360 and 362. Preferably, a single piece of material 364 can be used for both straps and most preferably, the material is a stretchable closed-cell foam rubber such as neoprene. The perimeter portions of single piece 364 which are adjacent to elastic strip 330 and aperture 350 are attached to main section 312 by stitching single piece 364 at protective perimeter layer 311.

Strap 360 has an area of loop material 361 for engagement with the area of hook material 363 located on strap 362.

The ankle brace is temporarily secured to a wearer's ankle in the following manner:

As shown in FIG. 16, the brace 310 is positioned so that elastic strip 330 is aligned with the wearer's Achilles tendon and aperture 350 is adjacent to the wearer's heel with the portion of main section 312 defined as "C" positioned below the heel.

Next, the end of strap 314 is inserted through slot 342 so that the strap is across the top portion of the foot. Once through slot 342 strap 314 is wrapped around the underside of the foot and engages hook material 352. Thereafter, strap 316 is wrapped about the foot to engage hook material 354. The assembly is then complete.

Once brace 310 is in position, straps 360 and 362 are pulled across the top surface of the ankle so that loop material 361 engages hook material 363 so that a desired level of fit and comfort is attained. Next, the end of strap 326 is inserted through slot 333 so that the strap is snug across the front of the wearer's limb. Once through slot 333, the strap 326 is wrapped around the back side of the limb and thereafter inserted through D-ring 318. Strap 326 is then wrapped back around the back side of the limb and engages hook material 328 to temporarily secure the top portion of my brace to the wearer's ankle.

It should again be noted that because the preferred choice of temporary attachment is hook and loop material, adjustments for comfort, snugness and fit can be made with relative ease.

It is to be realized that only preferred embodiments of the invention have been described and that numerous substitutions, modifications and alterations are permissible without departing from the spirit and scope of the invention as defined in the following claims.

What is claimed is:

1. An orthopaedic support device for providing support to a human joint comprising:

a substantially flat sheet of durable material for extending around a human joint, said sheet material being formed of leather, pack cloth, suede, nylon or neoprene and comprising a main section having a plurality of straps connected thereto and integral therewith, each of said straps having a distal end;

a plurality of reinforced aperture slots located in said main section, whereby each strap is received in one of said aperture slots;

a D-ring located on the distal end of half of said straps, which are capable of being passed through said reinforced aperture slots; and a temporary fastening means to temporarily secure said distal end of each of said straps to said main section once said distal end has been passed through said corresponding aperture slot comprising a first and second component which interact with each other, said first component being located on said main section and said second component being located on said straps near the distal end of said straps, wherein said temporary fastening means is selected from the group consisting of snaps, straps, hinges, stays or hook and loop material.

2. The orthopaedic support device of claim 1 where said durable sheet material is neoprene.

3. An orthopaedic wrist brace comprising:

a substantially flat sheet of durable material for extending around a human wrist, said sheet material comprising;

a main section comprising a durable outer layer, a non-abrasive inner layer and a protective perimeter layer for reinforcing a perimeter of said main section;

a plurality of straps connected and integral with said main section, each strap having a distal end, at least one strap positioned for wrapping about the fingers when in use, one strap positioned for wrapping about the forearm when in use, and one strap positioned for wrapping about the thumb when in use;

a thumb channel defined by said strap positioned for wrapping about the thumb and main section;

a pocket provided on said main section having an outer surface and an inner surface, a metallic brace member for further limiting wrist movement, which is removably positioned between the inner surface of said pocket and the durable outer surface of said main section;

a plurality of reinforced aperture slots located in said main section for receiving each of said straps for wrapping about the fingers when in use and straps for wrapping about the forearm when in use;

D-rings located on the distal end of half of said straps for wrapping about the fingers when in use and wrapping about the forearm when in use, which are capable of insertion through said aperture slots; and a temporary fastening means to temporarily secure said distal end of each of said straps to said main section comprising a first and second component which interact with each other, said first component being located on said straps near said main section and said second component being located near the distal end of said straps, wherein said temporary fastening means is selected from the group consisting of snaps, straps, hinges, stays or hook and loop material.

4. The wrist brace of claim 3 where said durable sheet material is neoprene.

* * * * *